(12) United States Patent
Sauers

(10) Patent No.: US 9,461,416 B2
(45) Date of Patent: Oct. 4, 2016

(54) LOW FORCE ELECTRICAL CONTACT ON METALIZED DEFORMABLE SUBSTRATES

(71) Applicant: Roche Diagnostics Operations, Inc., Indianapolis, IN (US)

(72) Inventor: Matthew C. Sauers, Indianapolis, IN (US)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 172 days.

(21) Appl. No.: 13/798,453

(22) Filed: Mar. 13, 2013

(65) Prior Publication Data

US 2014/0273549 A1    Sep. 18, 2014

(51) Int. Cl.
| | |
|---|---|
| *G01N 27/00* | (2006.01) |
| *H01R 13/00* | (2006.01) |
| *H01R 13/703* | (2006.01) |
| *H01R 12/50* | (2011.01) |
| *G01N 27/327* | (2006.01) |

(52) U.S. Cl.
CPC ...... *H01R 13/7039* (2013.01); *G01N 27/3273* (2013.01); *H01R 23/725* (2013.01)

(58) Field of Classification Search
CPC ............ H01R 13/7039; H01R 23/725; G01N 27/3273
USPC ..................................... 439/59–62, 152, 660
See application file for complete search history.

(56) References Cited

U.S. PATENT DOCUMENTS

| | | | | |
|---|---|---|---|---|
| 4,638,559 A | * | 1/1987 | McGonigal | 29/874 |
| 6,152,754 A | * | 11/2000 | Gerhardt et al. | 439/325 |
| 2004/0110423 A1 | * | 6/2004 | Shishikura et al. | 439/630 |
| 2007/0249921 A1 | | 10/2007 | Groll et al. | |
| 2009/0054737 A1 | * | 2/2009 | Magar et al. | 600/300 |
| 2009/0325205 A1 | | 12/2009 | Fujii et al. | |
| 2011/0143562 A1 | | 6/2011 | Wu et al. | |

FOREIGN PATENT DOCUMENTS

| | | |
|---|---|---|
| EP | 2141493 A1 | 1/2010 |
| JP | 2012018930 A | 1/2012 |
| KR | 101161322 B1 | 7/2012 |
| WO | WO-2005053525 A1 | 6/2005 |

* cited by examiner

*Primary Examiner* — Lyle Alexander
*Assistant Examiner* — Robert Eom
(74) *Attorney, Agent, or Firm* — Harness Dickey

(57) ABSTRACT

A system for measuring an analyte of interest in a biological fluid includes a test strip for receiving a sample of the biological fluid having multiple contacts formed thereon. A test device includes a circuit board having multiple conducting strips. A connector assembly is fixed to the circuit board and receives the test strip as the test strip moves in an insertion direction to a test position. The connector assembly includes a connector assembly body and multiple conductors. Each of the conductors includes a conductor contact body fixedly connected to the connector assembly body, and a contact arm integrally connected to the conductor contact body and freely extending entirely in the insertion direction. The contact arm is deflected when directly contacted by one of the multiple contacts of the test strip.

10 Claims, 6 Drawing Sheets

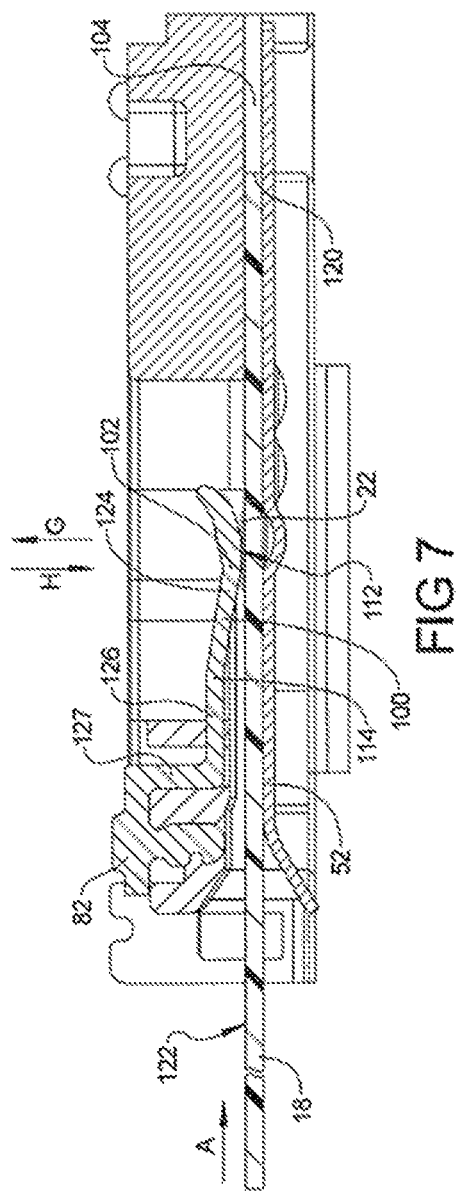

LOW FORCE ELECTRICAL CONTACT ON METALIZED DEFORMABLE SUBSTRATES

FIELD

The present disclosure relates to a testing apparatus for testing the presence or concentration of one or more substances in a biological fluid, and more particularly to such a device that includes one or more electrical connections between a test strip (bearing a sample of the biological fluid) and a test meter.

BACKGROUND

Measuring the concentration of substances, particularly in the presence of other substances, is important in many fields. This is especially true in medical testing and diagnosis. For example, the measurement of glucose in body fluids, such as blood, is crucial to the effective treatment of diabetes. A blood glucose meter is used as a diagnostic device to measure blood glucose levels of patients suffering from diabetes. Blood glucose meters use a test strip that receives a blood sample of the patient. The test strip has electrical contacts on the strip that are electrically contacted when the test strip is inserted into the meter. The meter determines a blood glucose level by measuring currents passed through the electrical contacts of the strip, and provides for readout of the glucose level.

A sample-receiving portion of the testing apparatus typically controls the geometry of the blood sample. In the case of blood glucose meters, for example, the blood sample is typically placed onto or into a disposable test strip that is inserted into a test meter. In the case of electrochemical test meters, electrical signals must be transferred between the meter and the test strip and vice versa. Known meters receive the test strip in an insertion direction that also engages the electrical strip conductors of the test strip with the electrical contacts of the meter. As the test strip is loaded by the user, the insertion motion is used to drive the electrical contacts of the test strip into engagement with the contacts of the meter.

Test system designers desire to minimize the size of the sample required for accurate measurement in order to improve the user experience. The resulting test sensor and test strip miniaturization has resulted in the use of thin film test strip patterns comprised of noble metals deposited on plastic substrates, such as by plating and subsequent laser ablation, to form the electrodes and associated connector contact pads of the test strip. Test strips can include for example of a thin film of a polymeric material such as a polyester which is coated such as by sputtering pure gold to a 50 nm thickness. Because the gold film is so thin and does not adhere well to the plastic film, the gold film coatings are prone to scratching by current commercially available connectors. Therefore, reducing abrasion between the test strip contact pad and meter connector contact wire is especially important in biosensor designs. Repeat insertions of the test strip (two to four times) can render these thin film-coated biosensors useless. Even the first-time insertion of the test strip into the test meter may cause some removal of these thin film coatings by the test meter connector. The result is a less reliable connection between the contact pad on a test strip and the connector contact wire in the test meter.

Present connectors used in blood glucose meters can include both a long extending first beam portion to provide flexibility and a second oppositely directed bent wire form at the contact end with the test strip. The bent wire form imparts residual stresses in the connector. The bent wire form also provides poor dimensional control at the clearance point where the test strip contacts the connector. The bent wire form is therefore commonly positioned closer to the test strip than necessary, requiring a greater force to displace and thereby also causing greater potential for removal of the gold layer.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

In one embodiment of the disclosure, a system for measuring an analyte of interest in a biological fluid includes a test device having a connector assembly receiving a test strip moved in an insertion direction to a test position. The connector assembly includes a connector assembly body. A conductor includes a conductor contact body fixedly connected to the connector assembly body and a contact arm integrally connected to the conductor contact body and extending entirely in the insertion direction.

In another embodiment, a system for measuring an analyte of interest in a biological fluid includes a test strip for receiving a sample of the biological fluid having multiple contacts formed thereon. A test device includes a circuit board having multiple conducting strips. A connector assembly is fixed to the circuit board and receives the test strip as the test strip moves in an insertion direction to a test position. The connector assembly includes a connector assembly body and multiple conductors. Each of the conductors includes a conductor contact body fixedly connected to the connector assembly body. A contact arm is integrally connected to the conductor contact body and freely extends entirely in the insertion direction. The contact arm is deflected when directly contacted by one of the multiple contacts of the test strip.

In a further embodiment of the disclosure, a system for measuring an analyte of interest in a biological fluid includes a test strip for receiving a sample of the biological fluid having multiple contacts formed thereon. A test device includes a circuit board having multiple conducting strips. A connector assembly is fixed to the circuit board and receives the test strip as the test strip moves in an insertion direction to a test position. The connector assembly includes a connector assembly body and a plate positioned to slidably receive the test strip between the plate and the connector assembly body. Multiple conductors each include a conductor contact body fixedly connected to the connector assembly body and a contact arm integrally connected to the conductor contact body and freely extending entirely in the insertion direction. The contact arm is deflected when directly contacted by one of the multiple contacts of the test strip. The contact arm has a contact portion positioned in a cavity created between an inward facing surface of the plate and an inner wall of the connector assembly body.

In further embodiments, a blood glucose measuring system includes a test strip for receiving a sample of the biological fluid having multiple contacts formed thereon. A test device includes a circuit board having multiple conducting strips. A connector assembly is fixed to the circuit board and receives the test strip as the test strip moves in an insertion direction to a test position. The connector assembly includes a connector assembly body and multiple conductors. Each of the conductors includes a conductor contact body fixedly connected to the connector assembly body, and a contact arm integrally connected to the conductor contact body and freely extending entirely in the insertion direction. The contact arm is deflected by an edge of the inserted test strip and a contact pad of the strip slides under the contact as the test strip is fully inserted. The contact arm has a deflectable beam portion divisible into two primary portions, including a first deflectable beam portion having a convexly curved contact portion and extending to a bend, and a second deflectable beam portion extending from the bend to a rigid beam portion.

In other embodiments, a system for measuring an analyte of interest in a biological fluid includes a test strip for receiving a sample of the biological fluid and having a contact formed thereon. A fluid analysis test device includes a connector for receiving the test strip as it moves in an insertion direction. The connector includes a beam created from a flat sheet aligned to directly contact a surface of the contact. The beam trails along the contact as the test strip moves in the insertion direction. Coined edges of the beam each define a bi-directionally curved surface minimizing a pressure area of a portion of the conductor in contact with the test strip.

In a further embodiment, a method is provided for minimizing contact between a test strip and a conductor of a biological fluid analyte measurement device.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

BRIEF DESCRIPTION OF THE DRAWINGS

FIG. 7 shows a cross sectional side elevational view similar to FIG. 6 further showing a test strip in an installed test position; and FIG. 8 shows a front cross sectional view taken at section 8 of FIG. 6.

Figure 1:
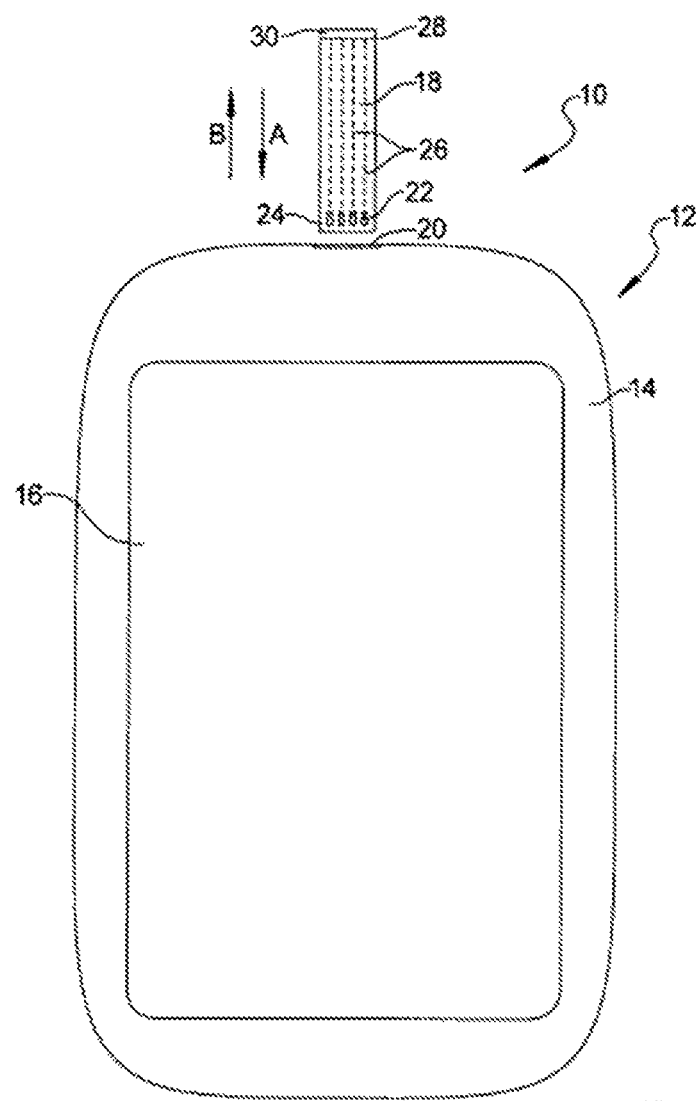
FIG. 1 shows a top plan view of a fluid analysis device having a low force electrical contact of the present disclosure.

Corresponding reference numerals indicate corresponding parts throughout the several views of the drawings. The drawings described herein are for illustrative purposes only of selected embodiments and not all possible implementations, and are not intended to limit the scope of the present disclosure.

DETAILED DESCRIPTION

Example embodiments will now be described more fully with reference to the accompanying drawings.

Referring now to FIG. 1, an exemplary biological testing system 10 includes a reusable testing meter or fluid analysis test device 12 having a body 14 with a data input/viewing window 16 which can display analysis test results and icons prompting the user for operation selections or to eject a test strip 18. The disposable test strip 18 is inserted in an insertion direction "A" through a slot 20 opening through body 14. Test strip 18 includes at least one contact and according to several aspects includes multiple contacts depicted as contact pads 22 (multiple such contacts are shown in FIG. 1 by way of example only) near an insertion end 24 of test strip 18. The contact pads 22 are connected via conductors 26 to electrodes 28 near a second end 30 of test strip 18. When a testing operation is complete test results are provided on data input/viewing window 16, and the test strip 18 is ejected in an ejection direction "B" from body 14.

Referring now to FIG. 2 and again to FIG. 1, the test strip 18 is slidably received in slot 20 which according to several aspects is provided in a first end 32 of body 14. According to several aspects, slot 20 can extend through a first body portion 34 such as an upper body portion of body 14. In other aspects (not shown) slot 20 can extend through a second body portion 36 such as a lower body portion of body 14. The first and second body portions 34, 36 are assembled and connected together after loading internal components of test device 12.

Figure 2:
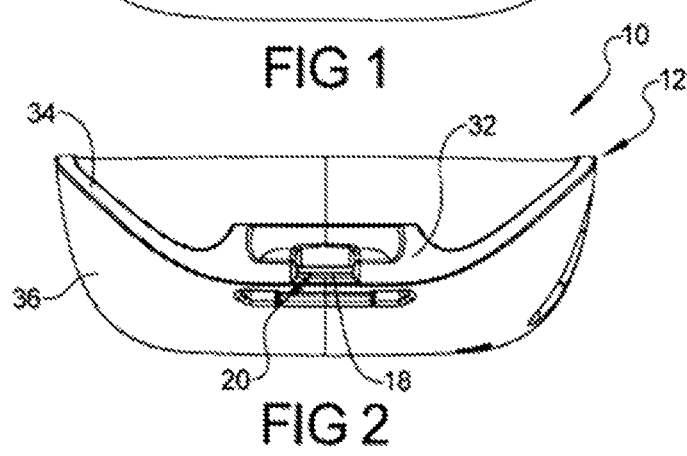
FIG. 2 shows an end elevational view of the device of FIG. 1.

Referring now to FIG. 3 and again to FIGS. 1-2, the first and second body portions 34, 36 are removed for clarity to illustrate an exemplary circuit board assembly 40. Circuit board assembly includes at least a circuit board 42 such as a printed circuit board. A connector assembly 44 is mounted to a face 46 of circuit board 42. The slot 20 is provided with connector assembly 44. In one aspect of the present invention, connector assembly 44 receives test strip 18 inserted through slot 20 into testing device 12 by sliding movement of the test strip 18 in the installation direction "A". In the configuration shown, test strip 18 is shown in a fully installed or test position within connector assembly 44. The connector assembly 44 includes a connector assembly body 48 which receives a metal plate 52 using multiple snap connectors 50 which will be described in greater detail in reference to FIG. 4. Plate 52 can include a bent or formed end portion 54 that helps align the test strip 18 with slot 20.

Figure 3:
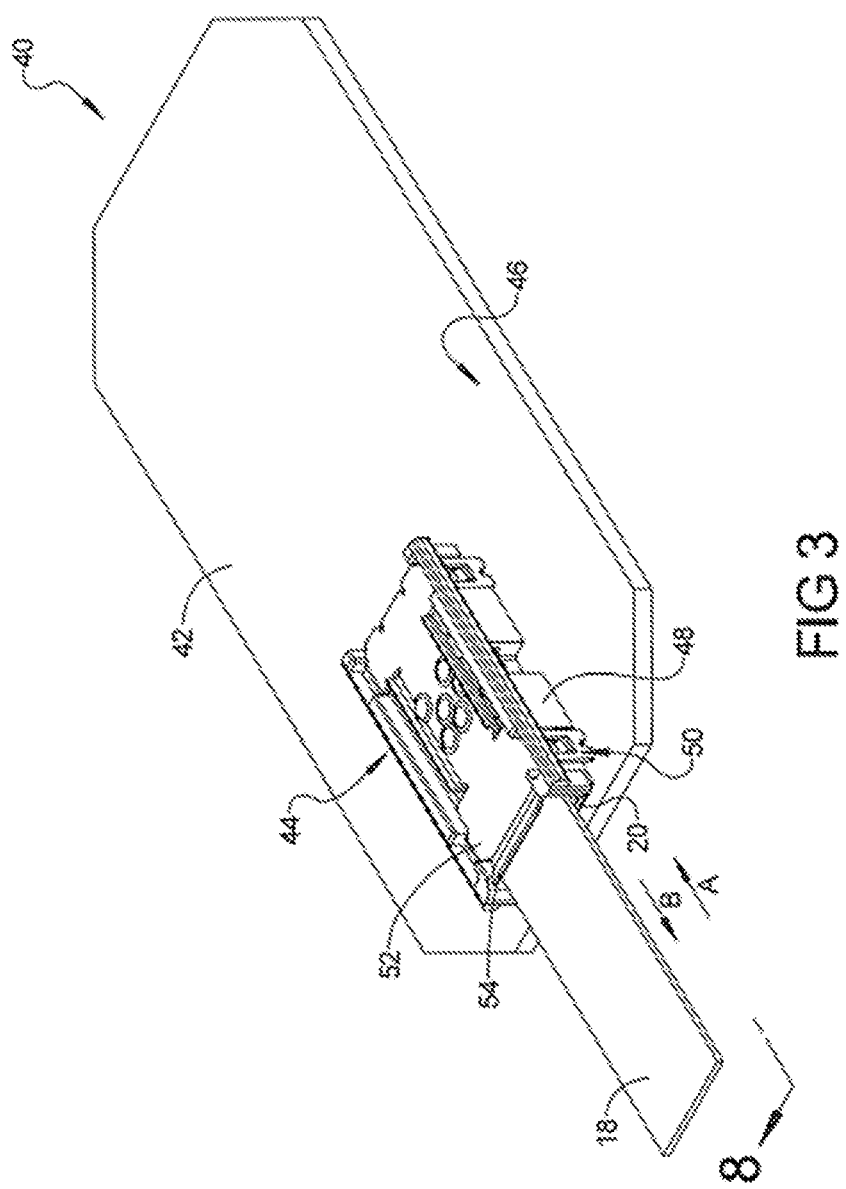
FIG. 3 shows a top left perspective view of a circuit board assembly of the present disclosure.

Referring now to FIG. 4 and again to FIGS. 1-3, slot 20 is defined by end portion 54 of plate 52 and further by opposed first and second side walls 56, 58 created of portions of the connector assembly body 48. According to several aspects connector assembly body 48 is a polymeric material molded for example in an injection molding process. An inlet longitudinal wall 60 spanning between the first and second side walls 56, 58 is parallel to and oppositely positioned with respect to end portion 54, thereby defining an enclosed rectangular shape of slot 20. Each of the first and second side walls 56, 58 can include an outwardly curving convex surface 62, 64 which also assist in the alignment of and reduce yawing motion of test strip 18 during entrance into slot 20.

Figure 4:
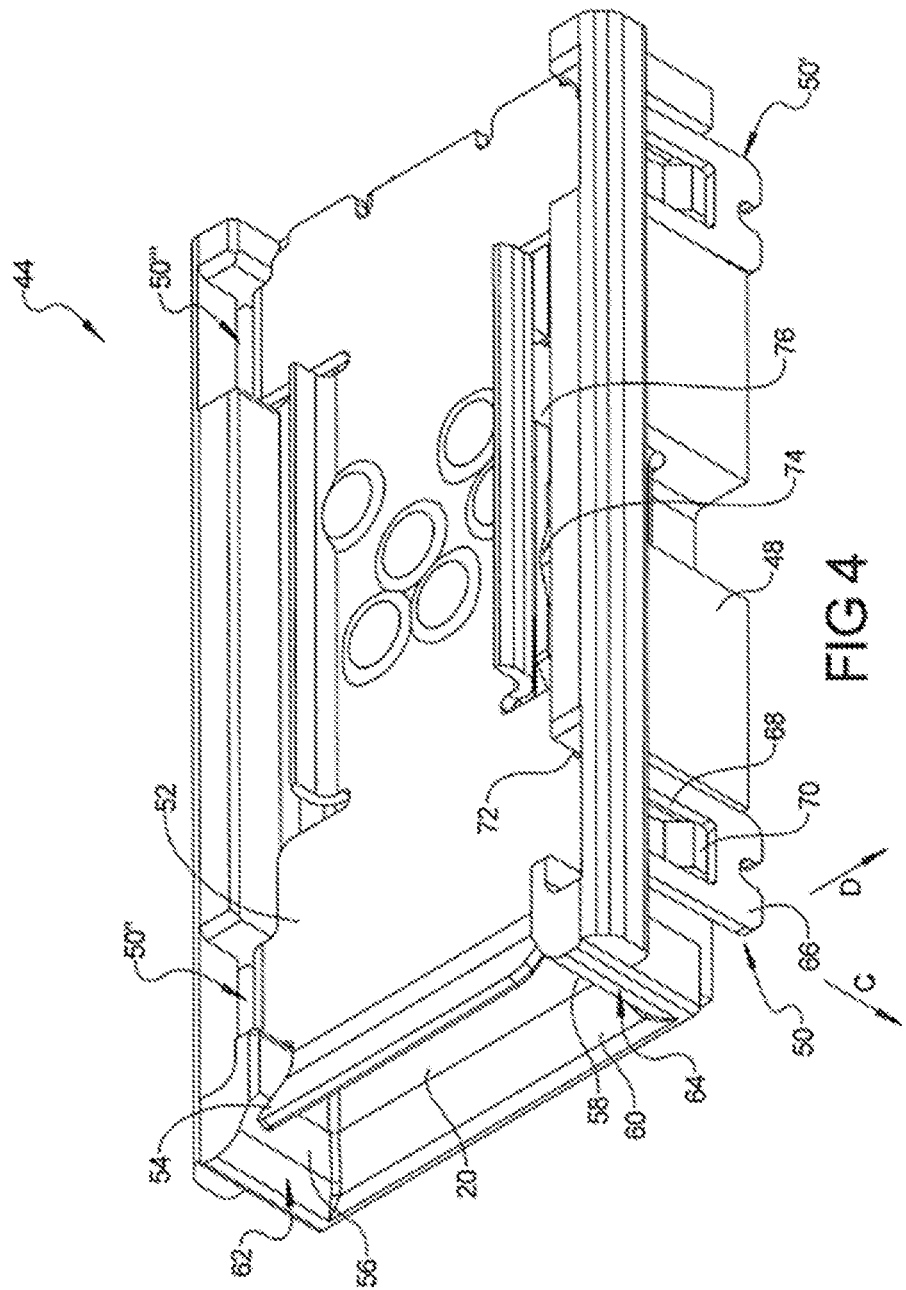
FIG. 4 shows a top left perspective view of a connector assembly of the present disclosure.

Four substantially identical snap connectors 50, 50', 50", 50'" are shown, however the quantity of snap connectors 50 is not limiting. Each of the snap connectors 50 includes a blade portion 66 which is an integral extension of plate 52 and is oriented substantially perpendicular to plate 52. Each blade portion 66 includes an elongated slot 68 which receives a tooth 70 integrally outwardly extending from connector assembly body 48. The plate 52 is coupled to connector assembly body 48 by insertion of the snap connectors 50, 50', 50", 50'" in cavities 72 created in connector assembly body 48 and pressing plate 52 in an installation direction "C". As each of the snap connectors 50, 50', 50", 50''', encounters the teeth 70, the snap connectors 50, 50', 50", 50''' deflect outwardly in an exemplary deflection direction "D" until the teeth 70 are received in each of the elongated slots 68. The snap connectors 50, 50', 50", 50''' return to their pre-deflected conditions with the teeth 70 locked in the corresponding elongated slots 68, thereby retaining plate 52 and connector assembly body 48. When connector assembly 44 is complete, a plurality of conductors 74 is provided which contact the individual contact pads 22 of test strip 18. In FIG. 4 only one of the conductors 74 is visible through an elongated opening 76 in plate 52.

Figure 5:
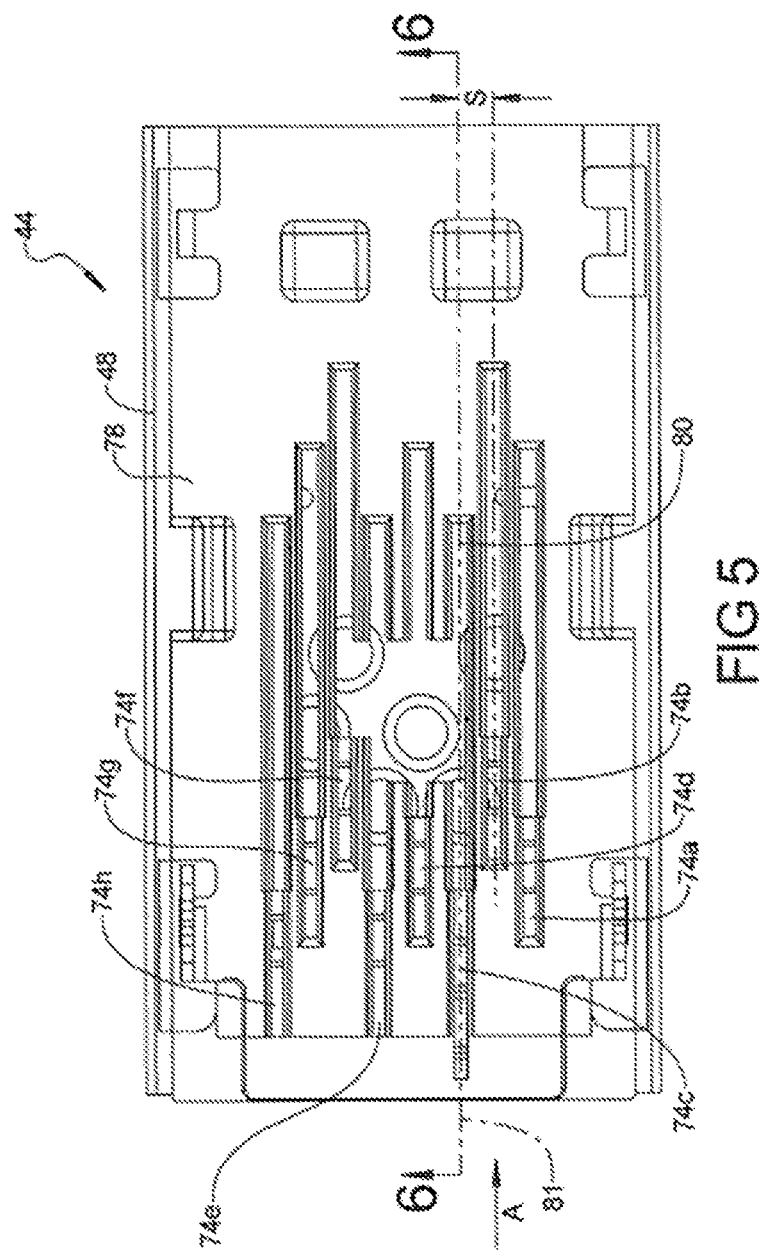
FIG. 5 shows a bottom plan view of the connector assembly of FIG. 4.

Referring now to FIG. 5 and again to FIGS. 1-4, when viewed from an opposite side of connector assembly 44 with respect to the view of FIG. 4, a bottom wall 78 is provided with multiple elongated slots 80. According to several aspects, there are eight elongated slots 80, each providing for a portion of an individual one of eight conductors 74 to extend outwardly of bottom wall 78. The connector assembly body 48 provides the multiple elongated slots 80 to each receive one of the multiple conductors 74 thereby sequentially spacing the conductors 74 from each other at a spacing "S" equaling a spacing between successive ones of the test strip contacts or contact pads 22. The eight conductors include conductors 74a, 74b, 74c, 74d, 74e, 74f, 74g, 74h. Each of the conductors 74 are fixed to an internal portion of connector assembly body 48 as will be described in greater detail in reference to FIG. 6. The quantity of conductors 74 is not limiting, and is determined by a corresponding quantity of contact pads 22 provided with test strip 18. A stepped longitudinal configuration of the conductors 74 can vary as shown depending on the location of the contact pads 22, and the desirability of separating the conductors to maintain electrical contact clearance between the individual conductors 74 when in contact with the contact pads 22. All of the conductors 74 are parallel to each other. The orientation of all of the conductors 74 as exemplified by a longitudinal axis 81 of conductor 74c is parallel to the insertion direction "A" throughout a length of each conductor 74. The staggered or stepped longitudinal configuration of the conductors 74 is also provided to allow the contact pads 22 to be wider than a pitch (spacing between individual contacts) of the connector such that a contact point to the test strip 18 can contact a wider target area.

Referring now to FIG. 6 and again to FIGS. 1-5, conductor 74c is presented as an exemplary installation. The remaining conductors 74 are similar in design and function and are therefore not further discussed. Conductor 74c includes a conductor contact body 82 having an extending portion 84 that extends freely outside of the elongated slot 80 that receives conductor 74c. An end face 86 of extending portion 84 makes direct contact with (for example using a soldered or pressed connection) a conducting strip 88 deposited on a face 90 of circuit board 42. Circuit board 42 includes a quantity of conducting strips 88 at least equal to a quantity of the conductors 74. An engagement body 92 is integrally connected to conductor contact body 82 and is oppositely directed with respect to end face 86. The engagement body 92 is pressed or otherwise fixed in a receiving cavity 94 created in the polymeric material of connector assembly body 48. The engagement body 92 includes at least one and according to several aspects first and second engagement ribs 96, 98 each extending outwardly away from the engagement body 92 to provide additional surface area for frictional contact and retention of engagement body 92.

A flexible beam or contact arm 100 extends away from engagement body 92 and is oriented in its entirety in the same direction as the test strip installation direction "A". According to several aspects, the contact arm is created from a flat sheet of material. Contact arm 100 provides a convexly curved portion 102 which is positioned in a cavity 104 created between an inward facing surface 106 of plate 52 and an inner wall 108 of connector assembly body 48. A gap "E" between inward facing surface 106 and inner wall 108 provides a sliding fit for receipt of test strip 18. According to several aspects, convexly curved portion 102 includes a convex curved surface 110 thereby providing a contact point 112 where electrical contact between contact arm 100 and test strip 18 occurs. A nominal clearance "F" is provided between contact point 112 and inward facing surface 106 of plate 52. Nominal clearance is less than gap "E" and according to several aspects is approximately 0.1 to approximately 0.15 mm. Contact arm 100 is formed by stamping a profile out of a sheet of metal therefore providing a profile without any bends compared to multiple or double bends provided in known conductor designs. The lack of any bending during forming eliminates residual stress from bending a wire-formed contact in contact arm 100, and thereby provides greater dimensional control of the location of contact point 112. A transition portion 114 extends away from the contact point 112. In addition, a shoulder 116 of conductor contact body 82 provides a repeatable direct contact location with a surface 118 of connector assembly body 48, which further improves dimensional control of the location of contact point 112.

Each contact arm 100 or flexible beam of all of the conductors 74 is integrally connected to its conductor contact body 82. All of the contact arms 100 individually freely extend away from the conductor contact body 82 entirely in the insertion direction "A" such that the contact arms define "trailing beams" that trail or drag on the test strip 18 as the test strip is displaced in the insertion direction "A". This orientation of the contact arms 100 minimizes the force required to ensure electrical contact is maintained with the contacts of the test strip 18. No portion of any of the contact arms 100 doubles back on itself or is directed opposite to or deviates away from the insertion direction "A".

Figure 6:
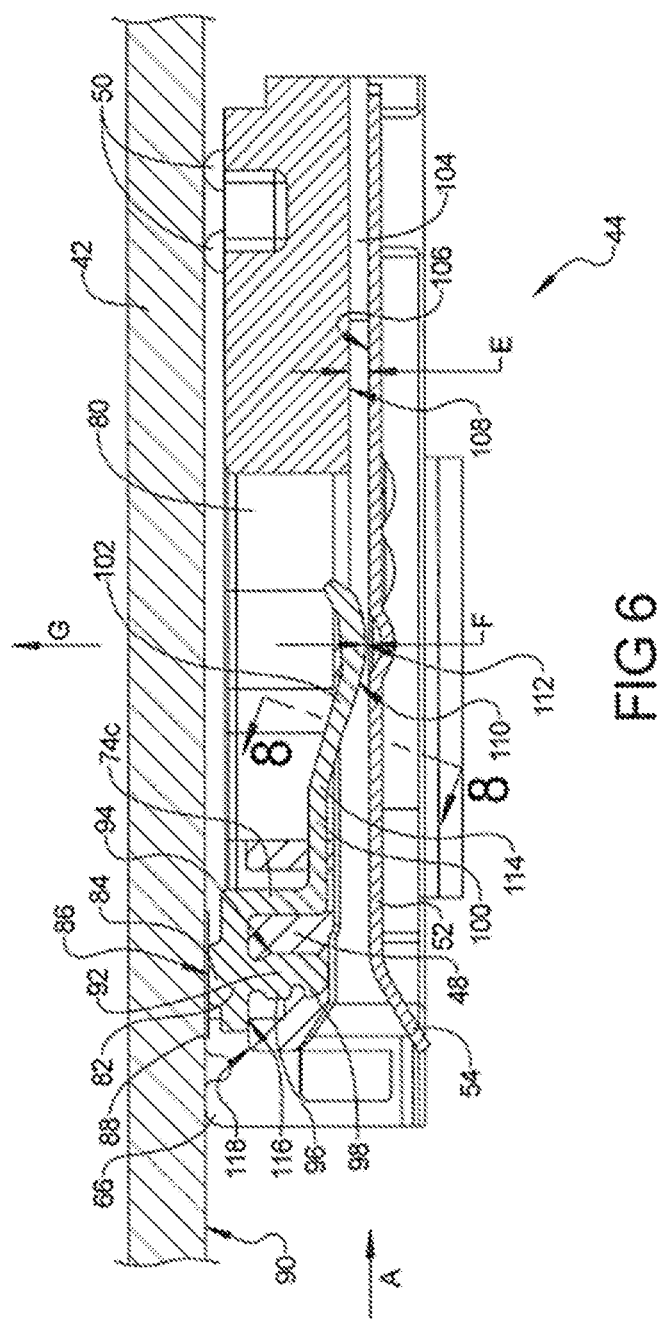
FIG. 6 shows a cross sectional side elevational view taken at section 6 of FIG. 5.

Referring now to FIG. 7 and again to FIG. 6, with the circuit board 42 removed for clarity, the test strip 18 is shown in the fully installed test position after insertion in the installation direction "A". Test strip 18 can contact an end wall 120 of cavity 104 defining a positive and repeatable stop and test position, to thereby positively position the contact pads 22 of test strip 18 which are located on a test strip surface 122 at the individual locations of the contact points 112 of each of the various conductors 74. A deflectable beam portion of contact arm 100 is divisible into two primary portions. The contact arm portion at contact point 112 is substantially non-deflectable. A first deflectable beam portion 124 therefore includes the transition region 114 extending away from convexly curved portion 102. A second deflectable beam portion 126 extends from the transition region 114 to a beam portion 127. The beam portion 127 is in direct contact with material of connector assembly body 48 and forms a portion of conductor contact body 82, and therefore can deflect substantially less than the transition portion 114 of contact arm 100. Elastic bending of first and second beam portions 124, 126 occurs during insertion of test strip 18. A reduced resistance to bending of contact arm 100 can be provided by increasing a length of second beam portion 126 and/or decreasing a thickness of contact arm 100. Contact arm 100 bending can therefore be tuned as desired. A force due to friction as test strip 18 is inserted and a shear force acting between the contact arm 100 and the test strip metallized areas (contact pads 22) are directly proportional to a down-force "H" provided by the contact arm 100 acting on the test strip 18. By reducing the down-force "H", the friction and shear forces are reduced compared to known conductors.

Referring now to FIG. 8 and again to FIGS. 6-7, the geometry of contact arm 100 is further controlled by use of an "eye-of-the-needle" coining process. This process provides rounded or coined edges 128 reducing surface irregularities, and a flat surface 130 opposed to a rounded surface 132. Drag features of contact arm 100 are thereby minimized, making micro-features on a perimeter surface 134 smaller than the size of particulates commonly present on the test strip 18 such as barium sulfate. The coined edges 128 of the beams or contact arms 100 each define a bi-directionally curved surface minimizing a pressure area of a portion of the conductor 74 in contact with the test strip 18.

Several benefits are provided by directing contact arm 100 only in the installation direction "A" away from its installed position at engagement body 92. These include: 1) a reduced friction between contact portion 102 and test strip 18 because all of the deflection of contact arm 100 in a deflection direction "G" occurs in only a single beam defined by contact arm 100, compared to multiple beams in known conductor designs; 2) the orientation of contact arm 100 facing in the installation direction "A" also reduces the chance of chatter occurring in the test strip 18 during installation, when integrity of the electrical contacts of the test strip 18 must be maintained to ensure test contact; 3) the "eye-of-the-needle" coining process used to create contact arm 100 fully coins the edges of contact arm 100, thereby creating a smooth bi-directionally curved surface such that particles such as barium sulfate particles in the polymeric material of the test strip 18 are not picked up by micro-features in contact arm 100 and dragged on the surface of the test strip 18; and 4) the nominal clearance "F" is increased compared to known conductor designs because the single beam design of contact arm 100 has greater dimensional control than known double or bent beam designs, allowing greater control of the location of contact point 112, thereby reducing the amount of deflection required to displace contact arm 100 which reduces friction during installation of test strip 18.

Biological testing systems 10 of the present disclosure offer several additional advantages. These advantages include a low contact force achieved using reduced stiffness contact arms 100, and using a reduced cross-section of the contact arms 100 achieved using a coining process to increase beam flexibility. A pressure applied to the contact arms 100 in lieu of an absolute force is relied on for enhanced electrical contact, thereby creating a distributed contact load or pressure load. This permits a reduced pressure contact area (an area of contact point 112) to achieve a desired contact pressure in a reduced area, and a reduction in a sliding friction area, which reduces the possibility of gouging the test strip 18. Still further, a square shape of the contact arms 100 permits angular displacement normal to a bending plane of the conductor 74 so the contact arms 100 can "ski-around" or displace around larger portions of impurities present in the test strip 18. Yet further, the contact arms 100 are oriented to drag the test strip surface 122 upon entry thereby allowing stuttering or chatter only on extraction of the test strip 18, with regard to the barium sulfate particles, thereby improving the overall contact path.

Biological testing systems 10 of the present disclosure can be used in meters by individual users having personal test meters. Biological testing system 10 of the present disclosure can also be incorporated in commercial devices such as hospital meters, for example rechargeable test meters recharged by installation in a base unit, and/or blood glucose meters such as ACCU-CHEK® Inform System glucose meters manufactured by Roche Diagnostics. Although the test strips used by such hospital and glucose test meters can be configured differently from the test strips identified herein to conform to the requirements of the test and/or test meter, the biological testing system 10 of the present disclosure will be similarly configured and function in a similar manner.

In addition, biological testing systems 10 of the present disclosure can also be incorporated in individual or commercial devices such as blood coagulant test meters, for example blood clotting time test meters such as the Coagu-Chek® XS System coagulant test meters manufactured by Roche Diagnostics. The test strips used by such blood coagulant test meters can be configured differently from the test strips identified herein to conform to the requirements of the test and/or test meter, however biological testing system 10 of the present disclosure will be similarly configured and function in a similar manner.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

What is claimed is:

1. A system for measuring an analyte of interest in a biological fluid, comprising:
    a circuit board having multiple conducting strips; and
    a connector assembly mounted on one side of the circuit board and configured to receive a test strip moved in an insertion direction to a test position, the connector assembly including:
        a connector assembly body;
        a metal plate having two or more snap connectors extending substantially perpendicular from the metal plate and towards the circuit board, wherein the metal plate is fastened to the connector assembly body via the snap connectors and cooperatively with the connector assembly body defines a slot that receives the test strip; and
        a conductor having:
            a conductor contact body mounted directly to the connector assembly body; and
            a contact arm integrally connected to the conductor contact body and freely extending entirely in the insertion direction.

2. The system for measuring an analyte of interest in a biological fluid of claim 1, wherein the connector assembly mounted to the circuit board defines a circuit board assembly and the circuit board assembly is retained in a test device.

3. The system for measuring an analyte of interest in a biological fluid of claim 2, further including:
    an extending portion of the conductor contact body; and
    a conducting strip of the circuit board directly contacted by the extending portion of the conductor contact body.

4. The system for measuring an analyte of interest in a biological fluid of claim 1, wherein each snap connector includes a blade portion having a slot formed therein and configured to receive a tooth extending outwardly from the connector assembly body when fastened thereto.

5. The system for measuring an analyte of interest in a biological fluid of claim 4, wherein the metal plate includes a formed end portion angularly oriented with respect to the metal plate to align a test strip.

6. The system for measuring an analyte of interest in a biological fluid of claim 4, further including:
an extending portion of the conductor contact body; and
the connector assembly body includes an elongated slot through which the extending portion freely extends.

7. The system for measuring an analyte of interest in a biological fluid of claim 1, further including:
a test strip for receiving a sample of the biological fluid having a contact formed thereon; and
the contact arm aligned to directly contact the contact of the test strip.

8. The system for measuring an analyte of interest in a biological fluid of claim 7, wherein the contact arm defines a beam trailing along the contact as the test strip moves in the insertion direction.

9. The system for measuring an analyte of interest in a biological fluid of claim 1, wherein the conductor having a rounded surface facing away from the circuit board and formed by a coining process, thereby minimizing a surface area of the conductor in contact with the test strip.

10. The system for measuring an analyte of interest in a biological fluid of claim 1 wherein the connector assembly includes multiple conductors and the connector assembly body includes multiple elongated slots each receiving one of the multiple conductors thereby sequentially spacing the conductors from each other at a spacing equaling a spacing between successive ones of the test strip contacts.

* * * * *